United States Patent [19]

Roberts et al.

[11] 4,393,214

[45] * Jul. 12, 1983

[54] PREPARATION OF 2-CHLORO-5-TRIFLUOROMETHYLPYRIDINE AND 2-CHLORO-5-PERCHLOROFLUOROMETHYLPYRIDINES

[75] Inventors: Norman L. Roberts, Walton; Graham Whitaker, Frodsham, both of England

[73] Assignee: Imperial Chemical Industries PLC, London, England

[*] Notice: The portion of the term of this patent subsequent to Sep. 8, 1998, has been disclaimed.

[21] Appl. No.: 243,428

[22] Filed: Mar. 13, 1981

Related U.S. Application Data

[63] Continuation of Ser. No. 143,479, Apr. 22, 1980, Pat. No. 4,288,600, which is a continuation-in-part of Ser. No. 95,678, Nov. 19, 1979, abandoned.

[30] Foreign Application Priority Data

Dec. 7, 1978 [GB] United Kingdom ............... 47583/78

[51] Int. Cl.³ .......................................... C07D 213/26

[52] U.S. Cl. .................................... 546/345; 546/346; 204/158 HA

[58] Field of Search .............................. 546/345, 346; 204/158 HA

[56] References Cited

U.S. PATENT DOCUMENTS

| | | | |
|---|---|---|---|
| 3,418,323 | 12/1968 | Johnston et al. | 546/345 |
| 3,420,833 | 1/1969 | Taplin | 546/180 |
| 3,424,754 | 1/1969 | Taplin | 546/345 |
| 3,732,230 | 5/1973 | Brewer et al. | 546/180 |
| 3,925,313 | 12/1975 | Kojima et al. | 528/26 |
| 4,045,499 | 8/1977 | Klein et al. | 568/734 |
| 4,257,857 | 3/1981 | Whittaker et al. | 204/158 HA |
| 4,309,548 | 1/1982 | Wilson et al. | 546/345 |

*Primary Examiner*—Alan L. Rotman
*Attorney, Agent, or Firm*—Cushman, Darby & Cushman

[57] ABSTRACT

2-chloro-5-trifluoromethylpyridine or a 2-chloro-5-perchlorofluoromethylpyridine is prepared by chlorination of 3-trifluoromethylpyridine or a 3-perchlorofluoromethylpyridine respectively in the vapor phase at a temperature in the range from 100° C. to 500° C.

4 Claims, No Drawings

PREPARATION OF 2-CHLORO-5-TRIFLUOROMETHYLPYRIDINE AND 2-CHLORO-5-PERCHLOROFLUOROMETHYL-PYRIDINES

This is a continuation of application Ser. No. 143,479, filed Apr. 22, 1980, now U.S. Pat. No. 4,288,600, which is a continuation-in-part of application Ser. No. 95,678, filed Nov. 19, 1979, and now abandoned.

This invention relates to the preparation of 2-chloro-5-trifluoromethylpyridine and 2-chloro-5-perchlorofluoromethylpyridines.

2-chloro-5-trifluoromethylpyridine and 2-chloro-5-perchlorofluoromethylpyridines are desirable intermediates for use in the preparation of compounds having herbicidal activity, for example in the preparation of herbicidal pyridine compounds described in U.K. Application No. 2 002 368A.

In co-pending U.S. application Ser. No. 10,598 is described a method of partial chlorination of 3-methylpyridine to give products containing a single chlorine atom in the pyridine ring and either two or three chlorine atoms as substituents in the methyl group. Among the products of the process there described is 2-chloro-5-trichloromethylpyridine, which may subsequently be fluorinated to yield 2-chloro-5-trifluoromethylpyridine or 2-chloro-5-perchlorofluoromethylpyridines (for example 2-chloro-5-chlorodifluoromethylpyridine).

In the partial chlorination of 3-methyl pyridine the desired 2-chloro-5-trichloromethylpyridine is, however, accompanied by substantial proportions of other partially-chlorinated derivatives which it can be difficult to separate from the desired product; this may lead to waste of material in the route to 2-chloro-5-trifluoromethylpyridine or 2-chloro-5-perchlorofluoromethylpyridines from 3-methyl pyridine via 2-chloro-5-trichloromethylpyridine.

We have now found that 2-chloro-5-trifluoromethylpyridine and 2-chloro-5-perchlorofluoromethylpyridines may selectively be prepared by chlorination of 3-trifluoromethylpyridine or a 3-perchlorofluoromethylpyridine respectively. Furthermore, the separation of the desired product from the by-products may usually be achieved more readily than separation of 2-chloro-5-trichloromethylpyridine from the by-products obtained in the chlorination of 3-methylpyridine.

According to the present invention there is provided a process for the preparation of 2-chloro-5-trifluoromethylpyridine or a 2-chloro-5-perchlorofluoromethylpyridine characterised in that 3-trifluoromethylpyridine or a 3-perchlorofluoromethylpyridine respectively is chlorinated in the vapour phase at a temperature in the range from 100° C. to 500° C., provided that when the temperature is below 250° C. the chlorination is carried out in the presence of ultra-violet radiation.

It is preferred to use at least 1 mole of chlorine per mole of 3-trifluoromethylpyridine on 3-perchlorofluoromethylpyridine. The vapour phase chlorination process is preferably carried out at a temperature in the range from 300° C. to 450° C. The preferred proportion of chlorine will depend upon the reaction temperature. In general it is preferred to use at least 0.5 mole of chlorine (for example from 0.5 to 10 moles, especially from 1 to 6 moles) per mole of 3-trifluoromethylpyridine, or 3-perchlorofluoromethylpyridine, but at relatively high temperatures, for example at temperatures above 400° C., the use of more than about 2 moles of chlorine per mole of 3-trifluoromethylpyridine or 3-perchlorofluoromethylpyridine may increase the proportion of products containing two or more chlorine atoms as substituents in the pyridine ring.

The vapour-phase chlorination is preferably carried out in the presence of a diluent; this may be inorganic, for example nitrogen and/or steam, but is preferably organic. When an organic diluent is used, this is preferably a compound which is inert towards chlorine (for example carbon tetrachloride, which is the diluent especially preferred) or a compound such that any reaction with chlorine yields a product which is inert to further chlorination (for example chloroform, which may yield carbon tetrachlorine).

When a gaseous diluent is used the 3-trifluoromethylpyridine or 3-perchlorofluoromethylpyridine starting material may be vapourised in the stream of diluent vapour which serves as a carrier gas; when a liquid diluent is used, the starting material may be dissolved in the liquid diluent and the resulting solution may then be vaporised as a whole.

In the vapour-phase chlorination, convenient residence times of the mixture in the reaction zone are, for example, between 10 and 30 seconds, but higher or lower residence times may be used.

The desired 2-chloro-5-trifluoromethylpyridine or 2-chloro-5-perchlorofluoromethylpyridine may be recovered from the reaction products by methods conventional in the art, for example fractional distillation and fractional crystallization.

The invention is illustrated by the following Examples.

EXAMPLE 1

A solution of 3-trifluoromethylpyridine in carbon tetrachloride was fed to a packed vaporiser maintained at a temperature of 300° C. The issuing vapours were passed to a vertical glass tubular reactor of 10 cm bore held at a temperature of 380° C. where they were mixed with a stream of chlorine. The residence time was 10.5 seconds.

The initial reaction mixture contained 3.5 moles of chlorine and 48 moles of carbon tetrachloride per mole of 3-trifluoromethylpyridine.

The gaseous reactor effluent over a period of 1 hour was condensed and the condensate was found by gas-liquid chromatography, mass spectrometry and nuclear magnetic resonance, to contain 2-chloro-5-trifluoromethylpyridine as the major product together with 2-chloro-3-trifluoromethylpyridine and 2,6-dichloro-3-trifluoromethylpyridine as by-products. The yields, determined by $^{19}F$ nuclear magnetic resonance using pure 2-fluoro-5-trifluoroethylpyridine as internal standard, were as follows:

2-chloro-5-trifluoromethylpyridine: 67%
2-chloro-3-trifluoromethylpyridine: 11%
2,6-dichloro-3-trifluoromethylpyridine: 7%

EXAMPLE 2

The procedure of Example 1 was repeated, except that the reaction temperature was 425° C. The yields were as follows:

2-chloro-5-trifluoromethylpyridine: 56%
2,6-dichloro-3-trifluoromethylpyridine: 25%
2-chloro-3-trifluoromethylpyridine: 4%

EXAMPLE 3

The general procedure was the same as in Example 1. The reaction mixture contained 1.1 mole of chlorine and 48 moles of carbon tetrachloride per mole of 3-trifluoromethylpyridine. The reaction temperature was 425° C. and the residence time was 25 seconds.

The yields were as follows:

2-chloro-5-trifluoromethylpyridine: 60%
2,6-dichloro-3-trifluoromethylpyridine: 18%
2-chloro-3-trifluoromethylpyridine: 7%

EXAMPLE 4

The general procedure was the same as in Example 1. The reaction mixture contained 6 moles of chlorine and 48 moles of carbon tetrachloride per mole of 3-trifluoromethylpyridine. The reaction temperature was 350° C. and the residence time was 16 seconds.

The yields were as follows:

2-chloro-5-trifluoromethylpyridine: 51%
2-chloro-3-trifluoromethylpyridine: 8%
2,6-dichloro-3-trifluoromethylpyridine: 3%
(unreacted 3-trifluoromethylpyridine 22%).

EXAMPLE 5

The general procedure was the same as in Example 1. The reaction mixture contained 3.5 moles of chlorine and 48 moles of carbon tetrachloride per mole of 3-trifluoromethylpyridine. The reaction temperature was 400° C. and the residence time was 10.5 seconds.

The yields were as follows:

2-chloro-5-trifluoromethylpyridine: 64%
2-chloro-3-trifluoromethylpyridine: 9%
2,6-dichloro-3-trifluoromethylpyridine: 14%

What is claimed is:

1. A process for the preparation of 2,6-dichloro-3-trifluoromethylpyridine which consists essentially of vaporizing 3-trifluoromethylpyridine and chlorinating the vaporized 3-trifluoromethylpyridine by contacting the same in the vapour phase with gaseous chlorine at a temperature in the range from 400° C. to 500° C. using at least one mole of chlorine per mole of 3-trifluoromethylpyridine.

2. A process according to claim 1 wherein the proportion of chlorine employed is from 1 to 6 moles per mole of 3-trifluoromethylpyridine.

3. A process according to claim 1 wherein the reaction mixture contains an organic diluent.

4. A process according to claim 3 wherein the diluent is carbon tetrachloride.

* * * * *